United States Patent
Umezawa et al.

(10) Patent No.: US 7,425,430 B2
(45) Date of Patent: Sep. 16, 2008

(54) PROBE FOR VISUALIZING PHOSPHORYLATION/ DEPHOSPHORYLATION OF PROTEIN AND METHOD OF DETECTING AND QUANTIFYING PHOSPHORYLATION/ DEPHOSPHORYLATION OF PROTEIN

(75) Inventors: Yoshio Umezawa, Tokyo (JP); Moritoshi Sato, Tokyo (JP); Takeaki Ozawa, Chiba (JP)

(73) Assignee: Japan Science and Technology Corporation, Saitama (JP)

( * ) Notice: Subject to any disclaimer, the term of this patent is extended or adjusted under 35 U.S.C. 154(b) by 84 days.

(21) Appl. No.: 10/296,313

(22) PCT Filed: Mar. 23, 2001

(86) PCT No.: PCT/JP01/02360

§ 371 (c)(1),
(2), (4) Date: Feb. 24, 2003

(87) PCT Pub. No.: WO02/077623

PCT Pub. Date: Oct. 3, 2002

(65) Prior Publication Data

US 2005/0049396 A1      Mar. 3, 2005

(51) Int. Cl.
*C07K 14/00* (2006.01)
*C12Q 1/42* (2006.01)

(52) U.S. Cl. .................. 435/69.7; 435/194; 435/7.7; 435/320.1; 435/325; 530/300; 530/303; 530/350; 530/387.1

(58) Field of Classification Search ............... 435/69.7, 435/194, 7.7, 320.1, 325; 530/303, 300, 530/350, 387.1
See application file for complete search history.

(56) References Cited

U.S. PATENT DOCUMENTS 6,441,140 B1 * 8/2002 Comb et al. ............. 530/387.1

FOREIGN PATENT DOCUMENTS

JP        11-56398        3/1999

OTHER PUBLICATIONS

Sato et al., A fluorecent Indicator for Tyrosine Phsophorylation-Based Insulin Signaling Pathway, Anal. Chem. 71, 3948-3954 (1999).*
Nagai et al.,, Nature Biotechnology, vol. 18, 313-316 (Mar. 2000).*
Hideyoshi Higashi et al., "Imaging of $Ca^{2+}$/calmodulin-dependent protein kinase II activity in hippocampal neurones", Membrane and Cellular Biophysics and Biochemistry, vol. 7, No. 15-17, pp. 2695-2700, Nov. 1996.
Motonobu Anai, et al., "Different Subcellular Distribution and Regulation of Expression of Insulin Receptor Substrate (IRS)-3 from Those of IRS-1 and IRS-2", The Journal of Biological Chemistry, vol. 273, No. 45, pp. 29686-29692, Nov. 6, 1998.

* cited by examiner

*Primary Examiner*—Chih-Min Kam
(74) *Attorney, Agent, or Firm*—Wenderoth, Lind & Ponack, L.L.P.

(57) ABSTRACT

As a versatile method of detecting and assaying intracellular protein phosphorylation and dephosphorylation that enables nondestructive monitoring as well as spatial and temporal analysis for living cells, animal bodies, plant bodies and the like, a probe for imaging protein phosphorylation and dephosphorylation, which comprises a tandem fusion unit composed of a substrate domain that contains a phosphorylation and dephosphorylation site, a linker sequence and a phosphorylation recognition domain, interposed between a donor chromophore and an acceptor chromophore that cause fluorescence resonance energy transfer, is used.

12 Claims, 8 Drawing Sheets
(1 of 8 Drawing Sheet(s) Filed in Color)

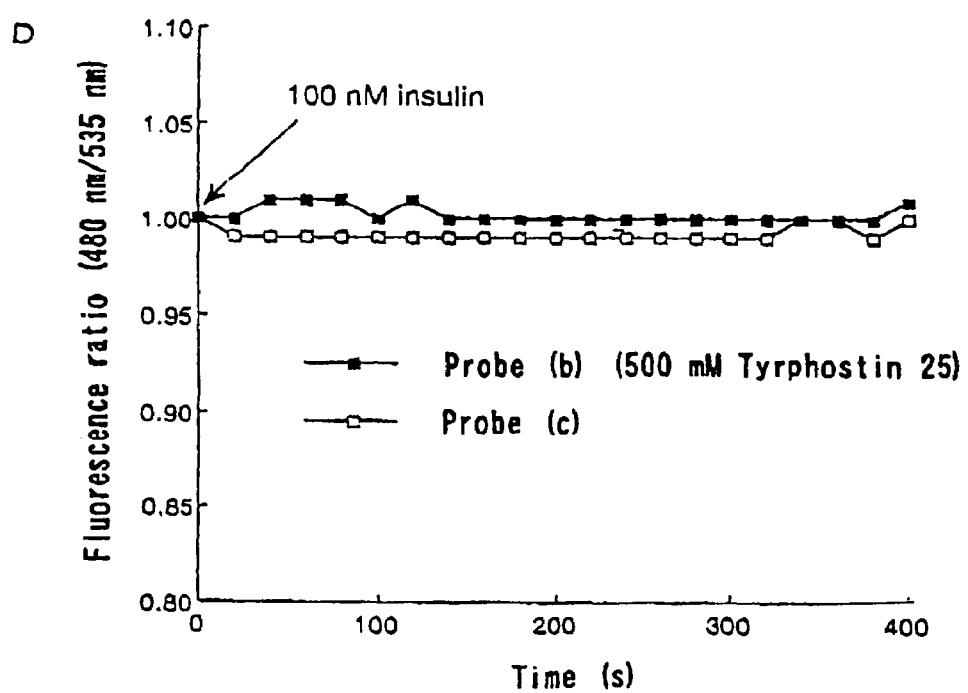
FIG. 4/1

F I G. 5
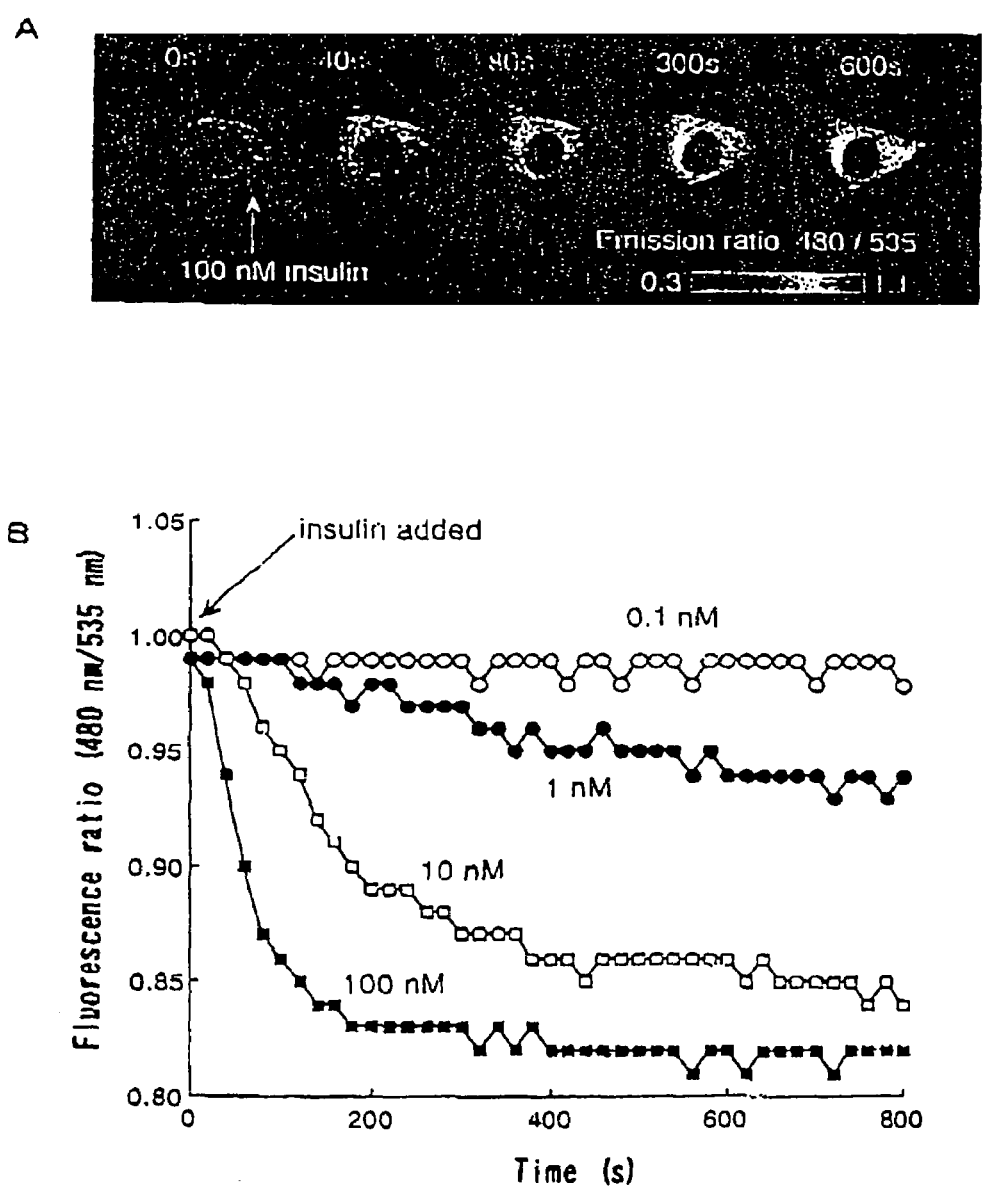

PROBE FOR VISUALIZING PHOSPHORYLATION/DEPHOSPHORYLATION OF PROTEIN AND METHOD OF DETECTING AND QUANTIFYING PHOSPHORYLATION/DEPHOSPHORYLATION OF PROTEIN

This application is a 371 of PCT/JP01/02360, filed Mar. 23, 2001.

TECHNICAL FIELD

The present invention relates to a probe for detecting and assaying protein phosphorylation and dephosphorylation. More particularly, the present invention relates to a probe for imaging protein phosphorylation and dephosphorylation comprising a substrate domain that contains a site that can be phosphorylated and a phosphorylation recognition domain, bound together by a linker sequence, interposed between a donor chromophore and an acceptor chromophore that cause fluorescence resonance energy transfer to occur, as well as a method for detecting and assaying protein phosphorylation and dephosphorylation using the same.

BACKGROUND ART

Protein phosphorylation by intracellular kinases is one of the most critical reactions in signaling within cells and is known to play important roles in various processes such as survival, proliferation, and differentiation of cells (*Cell* 100, 113-127 (2000)). Protein kinases catalyze transfer of the γ-phosphate of ATP and phosphorylation of hydroxyl groups of serines, threonines and/or tyrosines on the substrate proteins, and upon such phosphorylation, substrate proteins are subject to conformational changes due to negative charges of the phosphates, which subsequently triggers their enzymatic activation and interaction with their respective target proteins. Therefore, it is expected that by screening substances that enhance or suppress intracellular signaling triggered by protein phosphorylation and dephosphorylation, not only may diagnosis of diseases become possible, but important information for the development of new drugs may be obtained, as well.

Conventionally, analysis of signaling related to the kinase proteins has been preformed using means such as electrophoresis, immunocytochemistry, and kinase assay in vitro. However, these conventional methods are destructive methods and could not provide information on spatial and temporal analysis of signals from protein phosphorylation and dephosphorylation in living cells.

In contrast, unlike kinase signaling, second messenger signaling such as $Ca^{2+}$ (*Nature* 388, 882-887 (1997), inositol 1,4,5-triphosphate (*Science* 248, 1527-1530 (1999)), diacylglycerol (*J. Cell Biol.* 140, 485-498 (1998)), cyclic AMP (*Nature* 349, 694-697 (1997); *Nat. Cell Biol.* 2, 25-29 (1999)) and cyclic GMP (*Anal. Chem.* 72, 5918-5924 (2000)) has been visualized using fluorescent indicators; it has been reported that in such measurement methods, highly accurate spatial and temporal analysis of second messenger signaling in single living cells is made possible (*Curr. Opinion Neurobiol.* 10, 416-421 (2000)).

In recent years, along with probes for visualizing second messenger signaling, probes for visualizing kinase signaling in living cells have been studied and a few have been reported (*Anal. Biochem.* 195, 148-152 (1991); *NeuroReport* 7, 2695-2700 (1996); *FEBS Lett.* 414, 55-60 (1997); *Nat. Biotechnol.* 18, 313-316 (2000)). However, these imaging probes are all based on conformational changes of the substrate peptides themselves upon phosphorylation. Because controlling such conformational changes is impossible, such probes were only applicable to specific kinase signaling and lacked practicality.

Accordingly, the invention of the present patent application has been made in view of the above problems, and the object of the present invention is to provide a practical method for the detection and measurement of protein phosphorylation and dephosphorylation in living cells, animal bodies, plant bodies etc., that enables a non-destructive method for monitoring and further enables spatial and temporal analysis, thereby solving the problems of conventional techniques.

DISCLOSURE OF INVENTION

In order to solve the above-described problems, the present invention firstly provides a probe for imaging protein phosphorylation and dephosphorylation, which comprises a substrate domain that contains a site that can be phosphorylated and a phosphorylation recognition domain, bound together by a linker sequence, interposed between a donor chromophore and an acceptor chromophore that cause fluorescence resonance energy transfer to occur.

The present invention provides, secondly, the above probe for imaging protein phosphorylation and dephosphorylation, wherein the donor chromophore and the acceptor chromophore are fluorescent proteins each having different fluorescence wavelengths; thirdly, the above probe for imaging protein phosphorylation and dephosphorylation, wherein the donor chromophore and the acceptor chromophore that cause fluorescence resonance energy transfer to occur, are different color mutants of a green fluorescent protein; and fourthly, the above probe for imaging protein phosphorylation and dephosphorylation, wherein the mutants of the green fluorescent protein are a cyan fluorescent protein and a yellow fluorescent protein.

Furthermore, the present invention fifthly provides the above-described probe for imaging protein phosphorylation and dephosphorylation, wherein the site that can be phosphorylated in the substrate domain contains an amino acid residue selected from tyrosine, serine and threonine.

The present invention provides, sixthly, the probe for imaging protein phosphorylation and dephosphorylation, wherein the phosphorylation recognition domain is an endogenous domain selected from SH2 domain, phosphotyrosine binding domain or WW domain; further, seventhly, the probe for imaging protein phosphorylation and dephosphorylation, wherein the phosphorylation recognition domain is a single chain antibody obtained using the phosphorylated substrate domain as an antigen.

Further, the present invention eighthly provides any one of the above probe for imaging protein phosphorylation and dephosphorylation, which comprises a localization sequence at the terminal end.

Also, the present invention provides, ninthly, a method for screening substances that enhance or suppress protein phosphorylation, which comprises making the probe for imaging protein phosphorylation and dephosphorylation of any one of the first to eighth inventions coexist with a candidate substance, and measuring the change in efficiency of fluorescence resonance energy transfer (FRET) before and after addition of the candidate substance.

Further, tenthly, the present invention provides a method for screening substances that enhance or suppress protein phosphorylation, which comprises making the probe for imaging protein phosphorylation and dephosphorylation of any one of the first to eighth inventions, wherein the substrate domain has been phosphorylated, coexist with a candidate substance, and measuring the change in FRET efficiency before and after addition of the candidate substance.

The present invention eleventhly provides, the above method for screening substances that enhance or suppress protein phosphorylation, wherein the probe and che candidate substance are made to coexist by introducing the probe for imaging protein phosphorylation and dephosphorylation in to cells.

Still further, twelfthly, the present invention provides a method for assaying a substance that causes protein phosphorylation, which comprises introducing the probe for imaging protein phosphorylation and dephosphorylation of any of the first to eighth inventions into cells, and measuring the change in FRET efficiency before and after addition of the candidate substance.

And, thirteenthly, the present invention also provides a method for assaying a substance that causes protein dephosphorylation, which comprises introducing the probe for imaging protein phosphorylation and dephosphorylation of any one of the first to eighth inventions, wherein the substrate domain has been phosphorylated, and measuring the change in FRET efficiency before and after addition of the candidate substance.

The patent or application file contains at least one drawing executed in color. Copies of this patent or patent application publication with color drawings will be provided by the Office upon request and payment of the necessary fee.

BRIEF DESCRIPTION OF THE DRAWINGS

The patent or application file contains at least one drawing executed in color. Copies of this patent or patent application publication with color drawings will be provided by the Office upon request and payment of the necessary fee.

FIG. 5A is a representation of the pseudocolor images that shows the time course change of CFP/YFP (excitation at 440±10 nm) in the nucleus and the cytosol of the cells to which the probe for imaging protein phosphorylation and dephosphorylation that contains a nuclear-export signal sequence as shown in FIG. 2(d) were introduced, after stimulation with insulin.

FIG. 5B is a graph that shows the time course change of CFP/YFP (excitation at 40±10 nm) in the cytosol when the cells to which the probe for imaging protein phosphorylation and dephosphorylation of FIG. 2(d) were introduced were stimulated with insulin of various concentration.

BEST MODE FOR CARRYING OUT THE INVENTION

As described above, protein phosphorylation by intracellular kinases is one of the most important steps in intracellular signaling and participates profoundly in processes such as survival, proliferation, and differentiation of cells. Accordingly, protein phosphorylation and dephosphorylation are observed as a phenomenon related to the cause or certain symptoms of various diseases. In other words, if a method for detecting and assaying phosphorylation of specific proteins is realized, early diagnosis of various diseases may become possible. Moreover, the realization of a method for screening factors or substances that enhance or inhibit protein phosphorylation and dephosphorylation may contribute greatly to the discovery of substances relating to such diseases and the development of novel treatment drugs.

Figure 1:
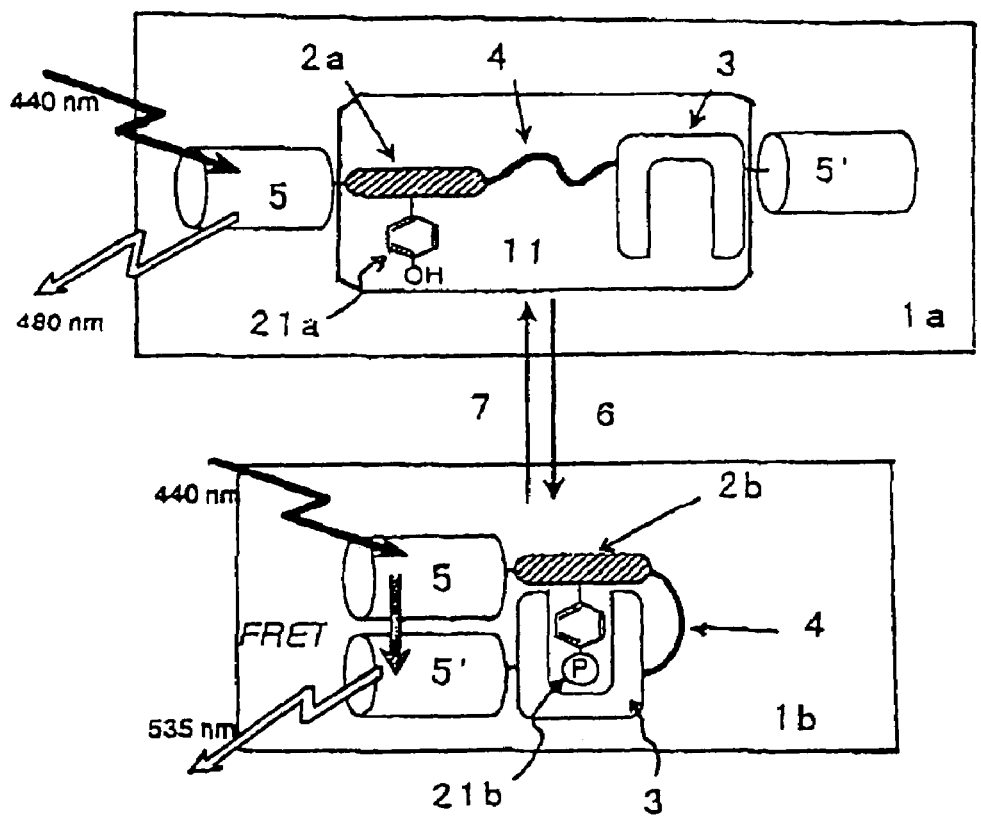
FIG. 1 is a scherntatic diagram that describes the construction and principle of the probe for imaging protein phosphorylation and dephosphorylation of the present invention 1 to 8 represent the following: (1a: probe for imaging protein phosphorylation and dephosphorylation (before phosphorylation), 1b: probe for imaging protein phosphorylation and dephosphorylation (after phosphorylation), 11: tandem fusion unit, 2a: substrate domain (before phosphorylation), 2b: substrate domain (after phosphorylation) 21a: phosphorylation site (before phosphorylation), 21b: phosphorylation site (after phosphorylation). 3: phosphorylation recognition site, 4: linker sequence, 5: donor chromophore, 5': acceptor chromophore, 6: phosphorylation substance, 7: dephosphorylation substance)

The probe for imaging protein phosphorylation and dephosphorylation of the present invention is a probe that makes visible and thereby enables the detection and assay of phosphorylation of protein by phosphorylating substances. The structure and principle of such probes for protein phosphorylation and dephosphorylation is shown in FIG. 1.

Specifically, the probe for imaging protein phosphorylation and dephosphorylation (1a) of the present invention comprises a tandem fusion unit (11) that comprises a substrate domain (2a), which contains a site that can be phosphorylated (21a) and a phosphorylation recognition domain (3) bound together by a linker sequence (4), interposed or sandwiched between a donor chromophore (5) and an acceptor chromophore (5') that cause fluorescence resonance energy transfer to occur.

For the probe for imaging protein phosphorylation and dephosphorylation (1a) of the present invention, for example, when the phosphorylation site (21a) of the substrate domain (2a) is phosphorylated by a phosphorylation substance (6), the adjacent phosphorylation recognition domain (3) recognizes it, and specifically interacts with the phosphorylated substrate domain (21a). In the probe for imaging protein phosphorylation and dephosphorylation (1b) wherein such an interaction occurred, the donor chromophore (5) and the acceptor chromophore (5') come into close proximity to each other; therefore, upon exposure to external light, excitation of the donor chromophore (5) followed by an energy transfer to the acceptor chromophore takes place, resulting in a change in efficiency of fluorescence resonance energy transfer (FRET). Thus, by detecting such change in FRET, phosphorylation (2b) of the substrate domain (2a) can be confirmed.

In a similar manner, when the probe for imaging protein phosphorylation and dephosphorylation (1b) containing a phosphorylated substrate domain (21b) coexists with a dephosphorylation substance (7), and the phosphorylated site of the substrate domain (2b) is dephosphorylated (21a), then interaction between the phosphorylation recognition domain (3) and the substrate domain (2b) disappears, which leads to the separation of the donor chromophore (5) and the acceptor chromophore (5'). By exposing external light, only the excitation of the donor chromophore (5) occur without energy transfer to the acceptor chromophore. Accordingly, dephosphorylation of the substrate domain (2b) can be detected from the change that appears in the FRET efficiency, using fluorescence analysis.

Each unit constituting the probe for imaging protein phosphorylation and dephosphorylation of the present invention is described more specifically. First, as described above, the tandem fusion unit (11) consists of the substrate domain (2a), the phosphorylation recognition domain (3) and the linker sequence (4) that bind them together. Here, the sequence or structure of the substrate domain (2a) is not restricted as long as it contains a site that can be phosphorylated (21a). The site capable of being phosphorylated (21a) usually contain is an —OH group, and natural amino acids such as tyrosine (Tyr) serine (Ser), threonine (Thr) and the like, as well as peptides to which an OH group is introduced by chemical modification may be exemplified.

Next, the phosphorylation recognition domain recognizes phosphorylation of the substrate domain (2a) and interacts specifically with the phosphorylated substrate domain (2b). The phosphorylation recognition domain may have any structure as long as it fulfills the above conditions. For example, endogenous domains such as SH2 domain, phosphotyrosine binding domain, WW domain and the like that are known to recognize specific phosphorylated substrates are applicable. Further, for detecting and assaying a substrate domain (2b) for which the phosphorylation recognition domain (3) that interacts with it is unknown, a single chain antibody may be prepared using the phosphorylated substrate domain (2b) as an antigen, and used as the phosphorylation recognition domain (3). By using such an antibody, a phosphorylation recognition domain (3) that interacts specifically with any desired phosphorylated substrate domain (2b) can be obtained, thereby enhancing the versatility of such probe for imaging protein phosphorylation and dephosphorylation.

The single chain antibodies that utilize the substrate domain (2b) as an immunogen may be prepared by known immunological means.

Next, in the probe for imaging protein phosphorylation and dephosphorylation of the present invention, the sequence and length of the linker sequence (4) are not limited as long as it enables appropriate flexibility and does not contain a site that can be phosphorylated. When the sequence (4) contains a site (21a) that can be phosphorylated, the site may be phosphorylated by a phosphorylation substance (6), which makes the accurate detection and assay of protein phosphorylation impossible. The linker sequence (4) may be any polypeptide or oligopeptide, which preferably has a chain length long enough to enable interaction between the phosphorylation recognition site (3) and the substrate domain (2b) upon phosphorylation of the substrate domain (2b), thereby approximating the donor chromophore (5) and the acceptor chromophore (5').

The probe for imaging protein phosphorylation and dephosphorylation of the present invention comprises the tandem fusion unit (11) of the above-described structure, interposed between a donor chromophore (5) and an acceptor chromophore (5') that cause fluorescence resonance energy transfer to occur; when the substrate domain (2a) is phosphorylated, a change in FRET is induced by the mechanism described previously. Such donor chromophore (5) and acceptor chromophore (5') may be selected from various fluorescent substances; particularly, fluorescent proteins are considered. The chromophores may be any substances that show fluorescence at different wavelengths upon exposure to external light, and cyan fluorescent protein is (CFP) and a yellow fluorescent protein (YFP), which are mutants of the green fluorescent protein (GFP), are preferable. CFP and YFP are particularly preferable; their mutated forms may be prepared in accordance with their use and utilized as the donor and/or acceptor chromophore.

In the above-described probe for imaging protein phosphorylation and dephosphorylation, the domain adjacent to the donor chromophore may be either of the substrate domain (2a) or the phosphorylation recognition domain (3). Since the preferable linking order differs depending on the structure or steric hindrance of these domains and linker sequence (4), the order may be selected according to the combination of the substrate domain (2a) and the phosphorylation recognition domain (3).

Further, the probe for imaging protein phosphorylation and dephosphorylation of the present invention may contain a variety of localization sequences at terminal end. Such localization sequences can recognize specific cells, specific regions in the cells or specific tissues, and therefore can localize the probe for imaging protein phosphorylation and dephosphorylation. Specifically, a nuclear-export-signal sequence or a plasma membrane binding sequence such as pleckstrin homology (PH) domain may be ligated as a localization sequence.

The probe for imaging protein phosphorylation and dephosphorylation of the present invention is as described above. But the method for its preparation is not particularly limited, and may be constructed by total synthesis; however, it is preferable to ligate each domain by known genetic engineering techniques such as polymerase chain reaction (PCR). Here, various restriction sites and the like may also be inserted.

In the invention of the present patent application, a method for screening substances that enhance or suppress protein phosphorylation using the above-described probe for imaging protein phosphorylation and dephosphorylation is also provided. In other words, if the substrate domain (2a) of the probe for imaging protein phosphorylation and dephosphorylation (1a) is phosphorylated when the probe for imaging protein phosphorylation and dephosphorylation of the present invention and a candidate substance coexist, protein phosphorylation is detected by the change in FRET under the mechanism previously described, thereby enabling the screening of substances that phosphorylate the substrate domain (2a). These candidate substances may act directly as a protein kinase that phosphorylate the protein, or may be substances that act at an early stage of intracellular signaling, that is, act as a protein kinase activating substance.

On the other hand, in order to confirm enhancement or suppression of dephosphorylation by a candidate substance and to screen a substance that enhance or suppress dephosphorylation, the substrate domain (2a) of the probe for imaging protein phosphorylation and dephosphorylation (1a) is first phosphorylated (2b), and the change in FRET that occur when in coexistence with a candidate substance is measured.

In the above-described method for screening substances that enhance or suppress phosphorylation and dephosphorylation, the probe for imaging protein phosphorylation and dephosphorylation (1a) maybe made to coexist with the candidate substance in a solution, for which, for example, the pH, salt concentration or the like is adjusted, or alternatively, the probe for imaging protein phosphorylation and dephosphorylation may be introduced into cells by genetic engineering techniques thereby made to coexist with the candidate substances. Here, the candidate substances may be resent outside the cells or may be incorporated into the cells; further, they may be pre-introduced into the cells by genetic engineering techniques. The candidate substances may also be enzymes, receptors or the like that exist in the cells.

Further, by using the probe for imaging protein phosphorylation and dephosphorylation of the present invention, the phosphorylating substances may be assayed, as well. In other words, by introducing the above probe for imaging protein phosphorylation and dephosphorylation into the cells, and measuring the changes in FRET efficiency before and after addition of the candidate substance, the amount of phosphorylation substances can be determined. For example, for substance A known to phosphorylate protein a, by observing the time course changes that occur in FRET in vitro when various concentrations of the phosphorylation substance A are in coexistence with the probe for imaging protein phosphorylation and dephosphorylation, and the time at which each FRET value reaches a plateau is predetermined. By creating a calibration curve of the FRET value and the concentration of substance A at that time, preparing the probe for imaging phosphorylation and dephosphorylation that contains protein a, which is phosphorylated by substance A, introducing such the probe into cells, and measuring the FRET value, substance A in the cells can be quantitated. Likewise, quantitative analysis of dephosphorylation substances may be performed in a similar manner.

As has been described previously, known genetic engineering techniques are applicable for as a method for introducing the probe for imaging protein phosphorylation and dephosphorylation into the cells. Specifically, an expression vector in which the probe for imaging protein phosphorylation and dephosphorylation is incorporated may be introduced into the cells by known methods such as electroporation, the calcium phosphate method, the liposome method, the DEAE dextran method. Thus, by introducing the probe for imaging protein phosphorylation and dephosphorylation into the cells and making the probe coexist with phosphorylation (or dephosphorylation) substances, an in vivo method for detecting and assaying protein phosphorylation (or dephosphorylation) that does not require the destruction of the cells is enabled.

The probe for imaging protein phosphorylation and dephosphorylation of the present invention is advantageous, not only for enabling the imaging of kinase signal transduction in single live cells at high spatial and temporal resolution, but also for being valuable in multi-cell analysis, which aims for the high-throughput screening of substances that regulate phosphorylation or dephosphorylation (*Science* 279, 84-88 (1998); *Drug Discovery Today* 4, 363-369 (1999)).

Further, in the probe for imaging protein phosphorylation and dephosphorylation of the present invention, a polynucleotide for the expression of the probe may be introduced into cells and used for the ontogenesis of non-human totipotent cells, thereby creating an animal or a progeny animal in which the probe for imaging protein phosphorylation and dephosphorylation and the phosphorylation (or dephosphorylation) substance coexist in all of its cells. These so-called non-human transgenic animals may be produced in accordance with known production methods (for example, *Proc. Natl. Aced. Sci. USA* 77, 7348-, (1980)). The non-human transgenic animals described above possess the probe for imaging protein phosphorylation and dephosphorylation in all of their somatic cells, and therefore, may be used to measure the concentration of phosphorylation (or dephosphorylation) substances in their cells or tissues; or by introducing candidates of phosphorylation (or dephosphorylation) substances, phosphorylation (or dephosphorylation) enhancing substances, and phosphorylation (or dephosphorylation) inhibiting substances, such as drugs an toxins, into their bodies, substances that show effect in cells or tissues may be screened.

Hereinafter, the present invention is described in further detail by the Examples with reference to the accompanying drawings. Of course, it should be needless to mention that the present invention is not limited to the following Examples and that various modifications may be made for the details.

EXAMPLES

Among various phosphorylation substances, nonreceptor tyrosine kinases and seine/threonine kinases function throughout the entire signal transduction cascades. On the other hand, tyrosine kinase receptors such as insulin receptor and hormone receptor function at the beginning of a number of signal transduction cascades.

In the following examples, a probe for imaging protein phosphorylation and dephosphorylation using insulin signal transduction protein was evaluated for the detection and assay of protein phosphorylation by insulin receptor, which is also a protein kinase.

<Preparation>

In the following examples, samples and reagents were used as follows:

Human insulin was purchased from Peptide Institute, Inc. (Osaka, Japan).

Ham's F-2 medium, fetal calf serum, Hank's balanced salt solution and LipofectAMINE 2000 reagent were obtained from Life Technologies (Rockville, Md.).

Tyrphostin 25 was purchased from Sigma Chemical Co. (St. Louis, Mo.).

Anti-phosphotyrosine antibody (PY20) andanti-β-subunit of human insulin receptor antibody were purchased from Santa Cruz Biotechnology, Inc. (Santa Cruz, Calif.).

Anti-GFP antibody were purchased from by Clontech (Palo Alto, Calif.).

Anti-rabbit IgG antibody labeled with Cy5 was obtained from Jacson ImmunoResearch Lab., Inc. (Pennsylvania, PA).

Other chemicals used were all of analytical reagent grade.

Example 1

Figure 2:
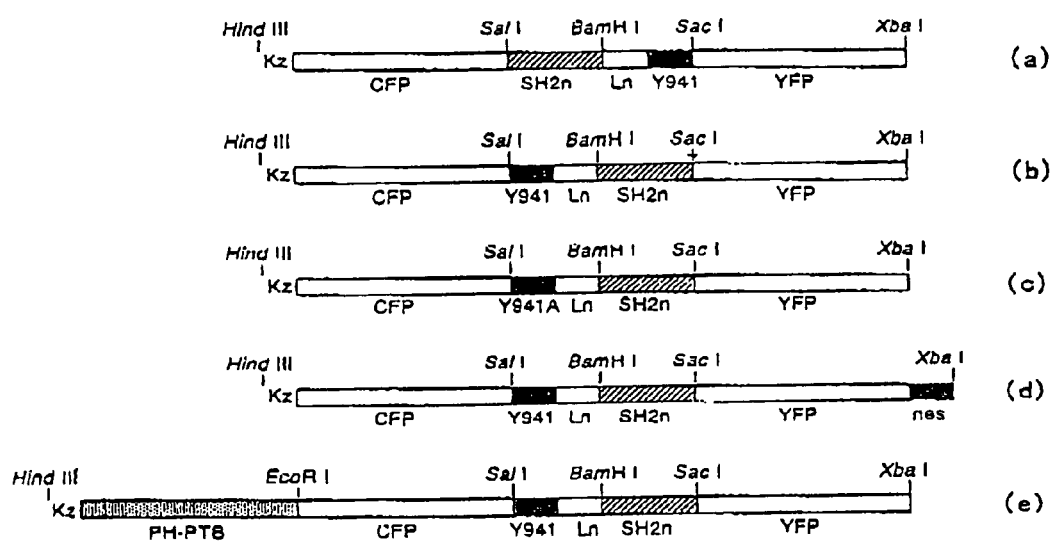
FIG. 2 is a schematic representation that shows specific structures of the probe for imaging protein phosphorylation and dephosphorylation constructed as an Example of the present invention.

Preparation of the Imaging Probe for the Detection of Protein Phosphorylation by Insulin Receptor (1) Plasmid Construction FIG. 2 is a representation of the specific structure of each probe for imaging protein phosphorylation and dephosphorylation that were prepared.

As shown in FIG. 2, the imaging probe was prepared so as to comprise a tandem fusion unit wherein a substrate domain containing a site to be phosphorylated and a phosphorylation recognition domain are bound together by a linker sequence, which is interposed between two mutants of the green fluorescent protein.

First, as a fluorescent protein, cyan fluorescent protein (CFP) and yellow fluorescent protein (YFP), which are different-colored mutants of the green fluorescent protein (GFP) originating from *Aequorea Victoria*, were used. Further, CFP was subjected to additional mutations of F64L/S65T/Y66W/N146I/M153T/V163A/N212K, and YFP was subjected to additional mutations of S65G/V68L/Q69K/S72A/T203Y.

Next, as a substrate domain, a tyrosine phosphorylation domain (Y941: SEQ ID NO: 1) derived from insulin receptor substrate-1 (IRS-1) was used. In this domain, insulin receptor phosphorylates the tyrosine residue 941 in an insulin dependent manner (*Mol. Cell Biol.* 13, 7418-7428 (1993)).

Next, as a phosphorylation recognition domain, an N-terminal SH2 domain (SH2n: $p85_{330-429}$) of p85 regulatory subunit of bovine phosphatidylinositol 3-kinase, which has been reported to bind to the phosphorylation substrate domain of IRS-1 protein, was chosen. (*J. Biol. Chem.* 267, 25958-25966)

As a linker sequence (Ln), the oligopeptide of SEQ ID NO: 2 was used.

Restriction sites shown in FIG. 2 were inserted to the cDNAs of CFP, YFP, the substrate domain and the phosphorylation recognition domain, using standard polymerase chain reaction (PCR). All cloning enzymes were purchased from Takara Biomedical (Tokyo, Japan). PCR fragments were sequenced using AB1310 genetic analyzer.

Further, cDNA encoding each probe for imaging protein phosphorylation and dephosphorylation was subcloned at Hind III and Xba I sites of a mammalian expression vector, pcDNA3.1 (+) (Invitrogen Co., Carlsbad, Calif.).

(2) Optimization of the Structure of the Probe for Imaging Protein Phosphorylation In the probe for imaging protein phosphorylation and dephosphorylation shown in FIG. 2(*a*) to (*e*), the order of SH2n and Y941 in the tandem fusion units of probe (a) and probe (b) are reversed.

In the present study, to determine which tandem fusion unit, that of probe (a) or probe (b), is more efficiently phosphorylated by insulin receptor, immunoblotting was performed using phosphotyrosine antibody after stimulating CHO-IR cells expressing probe (a) and probe (b) with 100 nM insulin.

First, IR cells were cultured in 6-well plates and were transfected with 2 μg of each plasmid containing probe (a) cDNA and probe (b) cDNA. CHO-HIR cells overexpressing human insulin receptor were cultured in Ham's F-12 medium supplemented with 10% fetal calf serum at 37° C. in 5% $CO_2$.

The cells were transfected with LipofectAMINE 2000 reagent. 12 to 24 hours after the transfection, the cells were spread onto glass bottom dishes, glass coverslips or plastic culture dishes.

Next, CHO-IR cells expressing probe (a) and probe (b) were stimulated with 100 nM of insulin for 20 minutes at 25° C.

The cells were lysed with an ice-cold lysis buffer (50 mM Tis-HCl, pH 7.4, 100 mM NaCl, 1 mM EDTA. 0.1% Triron X-100, 10 mM NaF, 2 mM sodium orthovanadate, 1 mM PMSF, 10 μg/mL pepstatin, 10 μg/mL leupeptin, 10 μg/mL aprotinin). The Imaging probes for protein phosphorylation were immunoprecipitated from the whole cell lysates of the CHO-IR cells with anti-GFP antibody for 2 hours at 4° C.

Protein G-Sepharose 4 FF beads were used to absorb the immunoprecipitates and then washed four times with an ice-cold washing buffer (50 mM Tris-HCl, pH 7.4, 100 mM NaCl, 1 mM EDTA, 0.1% Triron X-100, 10 mM NaF, 2 mM sodium orthovanadate, 1 mM PMSF, 10 μg/mL pepstatin, 10 μg/mL leupeptin, 10 μg/mL aprotinin). The samples were separated by SDS-polyacrylamide gel electrophoresis and analyzed by an immunoblotting method Using anti-phosphotyrosine antibody (PY20, 1:500 dilution).

Figure 3:
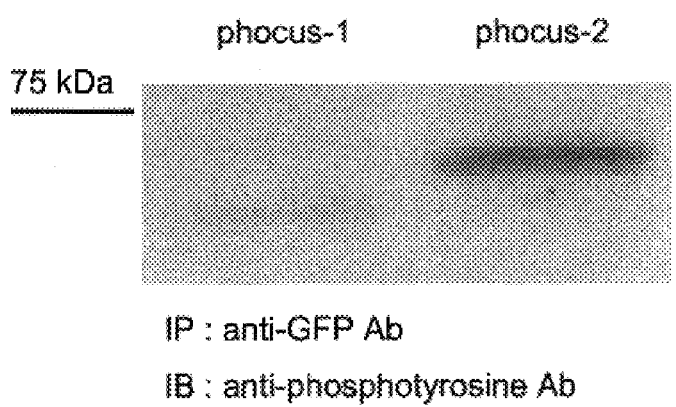
FIG. 3 shows the result of immunoblotting using a phosphotyrosine antibody, when the probe for imaging protein phosphorylation and dephosphorylation of FIGS. 2(a) and 2(b) were introduced into cells, as described in the Example of the present invention.

The result of the immunoblotting is shown in FIG. 3.

As shown in FIG. 3, probe (b) was well phosphorylated by insulin receptor, whereas probe (a) was poorly phosphorylated. This indicates that in the present experiment, the tandem fusion unit linked in the order shown in FIG. 2(*b*) is more effective as a probe for imaging protein phosphorylation than the tandem fusion unit linked in the order shown in FIG. 2(*a*).

In view of the x-ray crystal structure of insulin receptor in complex with a substrate peptide derived from IRS-1, the difference in the phosphorylation efficiency between probe (a) and probe (b) may be ascribed to the difference in steric effect.

In the following example, phosphorylation by insulin receptor was detected using probe (b).

Example 2

Detection of Phosphorylation Using the Probe for Imaging Protein Phosphorylation The increase in FRET efficiency after the phosphorylation of probe (b) by an insulin receptor was observed.

CHO-IR cells were transfected using the cDNA encoding probe (b) inserted in a mammalian expression vector, as described in Example 1.

After serum starvation with a serum-free medium, the culture medium was replaced with a Hank's balanced salt solution. 3 to 5 days after the transfection, the cells were observed at room temperature on a Carl Zeiss Axiovert 135 microscope with a cooled CCD camera MicroMAX (Roper Scientific Inc., Tucson, Ariz.) controlled by MetaFluor (Universal Imaging, West Chester, Pa.) in accordance with known methods (*Anal. Chem.* 72, 5918-5924 (1999)).

The exposure time at 440±10 nm excitation was 100 ms. The fluorescence images were obtained through 480±15 nm and 535±12.5 nm filters with a 40× oil immersion lens (Carl Zeiss, Jena, Germany).

Figure 4:
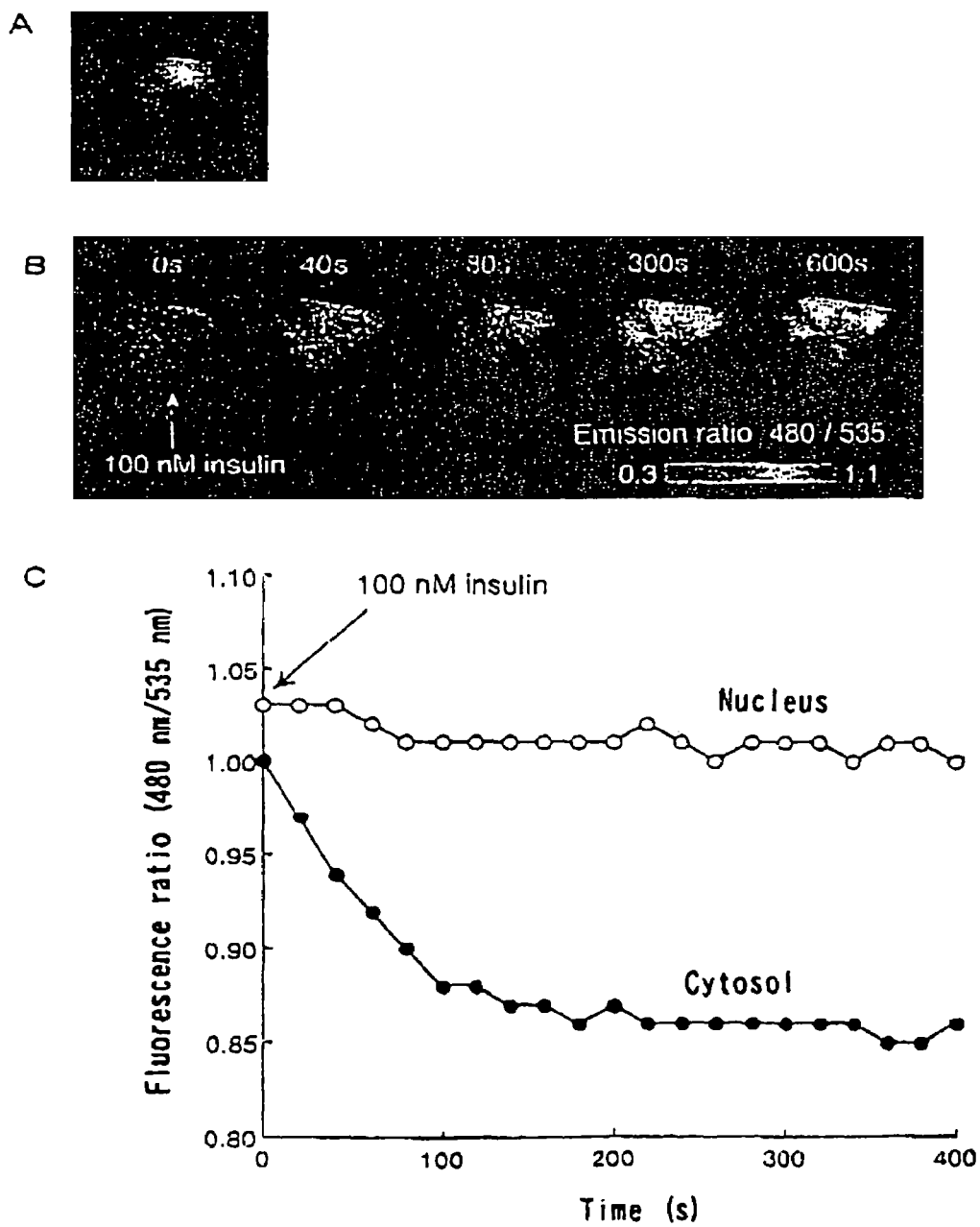
FIG. 4A is a fluorescence image of CFP after introducing the probe for imaging protein phosphorylation and dephosphorylation of FIG. 2(b) into cells, taken using an emission filter for CFP (480 nm±15 nm).
FIG. 4B is a representation of the pseudocolor images that shows time course change of emission ratios between CFP (480±15 nm) and YFP (535±12.5 nm) (herein after referred to as CFP/YFP) excited at 440+10 nm, when cells to which the probe for imaging protein phosphorylation and dephosphorylation of FIG. 2(b) were introduced were stimulated with insulin.
FIG. 4C is a graph that shows the time course change in CFP/YFP in the cytosol and the nucleus when excited at 440±10 nm, when the cells to which the probe for imaging protein phosphorylation and dephosphorylation of FIG. 2(b) were introduced were stimulated with insulin.
FIG. 4D is a graph that shows the time course change of CFP/YFP (excitation at 440±10 nm) in the cytosols of the cells to which the probe for imaging protein phosphorylation and dephosphorylation of FIG. 2(b) were introduced and treated with tyrphostin (an inhibitor of insulin receptor) (■), and the cells to which the probe for imaging protein phosphorylation and dephosphorylation of FIG. 2(c) were introduced (□), when stimulated with insulin.

FIG. 4A shows fluorescence microscope images of probe (b) expression cells, taken using an emission filter (480±15 nm) for CFP.

Probe (b) was found to be distributed uniformly in both the cytosolic compartment and in the nucleus.

Next, to evaluate the response of probe (b) for its phosphorylation, CHO-IR cells expressing probe (b) were stimulated with 100 nM of insulin in the same manner as described in Example 1.

FIG. 4B shows the time course changes of pseudocolor images of emission ratio of CFP at 480±15 nm to that of YFP at 535±12.5 nm excited at 440±10 nm.

Further, 4C shows the time courses of the emission ratio changes in the cytosol and in the nucleus. The administration of insulin caused a rapid and significant decrease in the cytosolic emission ratio for cells expressing probe (b), whereas the emission ratio in the nucleus showed no significant change (FIGS. 4B and 4C).

Furthermore, the insulin-induced change in emission ratio in the cytosol was completely suppressed when the cells were pretreated with 500 μM tyrphostin, an inhibitor for insulin receptor. As a negative control, CHO-IR cells expressing probe (c), in which tyrosine was replaced with alanine at the phosphoacceptor site of the substrate domain, were simulated with insulin; however, no significant change in the cytosolic emission ratio was observed (FIG. 4D).

The above results demonstrate that FRET from CFP to YFP increased upon phosphorylation of Y941 of probe (b) in the cytosolic compartment and subsequent binding of the phosphorylated Y941 with the adjacent phosphorylation recognition domain SH2n. Accordingly, this result indicates that probe (b) may be effective as a probe for imaging protein phosphorylation by insulin receptor in single live cells.

However, no significant change in FRET efficiency was observed in the nucleus; a more rigidly packed conformation of tyrosine-phosphorylated probe (b), compared to the floppy conformation of unphosphorylated probe (b) due to the existence of the linker sequence, may have restricted the traffic of the phosphorylated probe (b) through the nuclear pore, which forced the phosphorylated probe (b) to remain in the cytosolic compartment.

Example 3

Probe for Imaging Protein Phosphorylation containing a Nuclear-export-signal Sequence To prevent the probe for imaging protein phosphorylation from being transferred to the nucleus, where FRET changed did not occur upon insulin stimulation, as described in Example 2, a probe for imaging protein phosphorylation having a nuclear-export-signal sequence (d) was developed. AS the nuclear-export-signal sequence, a nuclear-export-signal sequence (nes; SEQ ID NO: 3) derived from human immunodeficiency virus protein, Rev (*EMBO J.* 16, 5573-5581), was linked to the terminal end of the probe for imaging protein phosphorylation.

Plasmid construction and transfection was done as described in Example 1.

No significant fluorescence was observed from the nucleus of the probe (d)-expressing cells. It was confirmed that the probe for imaging protein phosphorylation (d) was removed from the nucleus (FIG. 5A).

Further, upon stimulating the cells expressing probe (d) with 100 nM insulin, in the same manner as in Example 2, a progressive decrease in the cytosolic emission ratio was observed (FIG. 5A). No significant difference was observed in the time course of the probe (d) response, even when compared with that of probe (b) (FIG. 4B).

FIG. 5B shows the response of probe (d) to differing concentrations of insulin in CHO-IR cells. The accumulation rate of phosphorylated probe (d) by insulin receptor was increased in parallel with increasing insulin concentration. When the concentration of insulin was 0.1 nM, no accumulation of phosphorylated probe (d) was observed.

The relation between the emission ratio of probe (d) and insulin concentration was similar to the results reported for tyrosine phosphorylation of native IRS-1 protein in the cell, previously measured by autoradiography (*EMBO J.* 16, 5573-5581 (1997)).

The above results indicate that probe (d) is suitable as a probe for multi-cell analysis that utilize fluorescence multi-well plate reader, wherein the probe protein in the cytosol and the nucleus cannot be discriminated.

Hence, by using probe (d), high-throughput screening of anti-diabetic small molecules, such as L-783, 281 (*Nature* 318, 183-186 (1985); *Science* 284, 974-977 (1999)), which were reported to directly stimulate the kinase activity of insulin receptor, from thousands of candidate chemicals, may be realized.

Example 4

Probe for Imaging Protein Phosphorylation and Dephosphorylation Comprising a Living Cell Membrane Binding Sequence Signal transduction proteins, such as kinases, phosphatases and their substrates, are often localized in the cell and are organized to form domains of signal transduction by extracellular stimuli. This mechanism is thought to be a critical factor to determine the efficiency and specificity of signal transduction in the cell.

It has been known that IRS-1, which is the endogenous substrate protein for insulin receptor, contains a pleckstrin homology (PH) domain and a phosphotyrosine binding (PTB) domain to its N-terminal end (*Diabetologia* 40, S2-S17 (1997)).

The PH and PTB domain bind with the phosphoinositides of the cell membrane and with the juxtamembrane domain of insulin receptor, which is tyrosine-phosphorylated by insulin simulation, respectively (*Proc. Natl. Acad. Sci. USA* 96, 8378-8383). Thus, the concentration of IRS-1 is increased around insulin receptor at the plasma membrane upon insulin stimulation, which underlies efficient and selective phosphorylation of IRS-1 by insulin receptor (*J. Biol. Chem.* 270, 11715-11718 (1995)).

Then, probe (b) was fused with PH-PTB domain derived from the IRS-1 protein to construct the probe of FIG. 2(*e*).

CHO-IR cells expressing probe (e) were stimulated with 100 nM of insulin for 7 min at 25° C. The cells were fixed with 2% paraformaldehyde and were permeabilized with a phosphate-buffered saline containing 0.2% Triton X-100 for 10 min. After 45 min of incubation with rabbit anti-β subunit of human insulin receptor antibody (1:100 dilution), the cells were washed with a phosphate-buffered saline containing 0.2% fish skin gelatin and incubated with anti-rabbit IgG antibody labeled with Cy5 (1:500) for 30 min.

The coverslips were mounted onto the slide and observed with a confocal laser scanning microscope (LSM510, Carl Zeiss).

Figure 6:
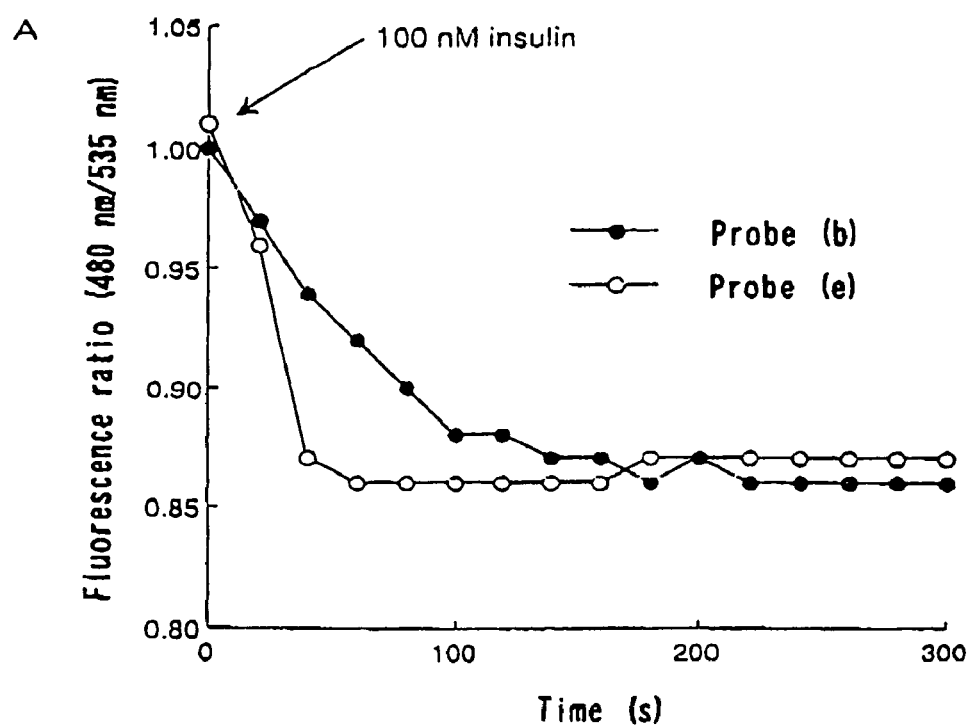
FIG. 6A is a graph that shows the time course change of CFP/YFP (excitation at 40±10 nm) in the cytosol when the cells to which the probe for imaging protein phosphorylation and dephosphorylation of FIG. 2(b) and FIG. 2(e) were introduced were stimulated with insulin.
FIG. 6B is a representation of the confocal laser fluorescence image that confirms the co-localization of the probe for imaging protein phosphorylation and dephosphorylation of FIG. 2(e) and the insulin receptor in the cells to which the probe for imaging protein phosphorylation and dephosphorylation of FIG. 2(e) were introduced, when stimulated with insulin.

FIG. 6A shows a comparison of the cytosolic emission ratio change for probe (e) and that for probe (b) in CHO-IR cells when stimulated with 100 nM insulin. Although the rate of the cytosolic emission ratio change for probe (e) was significantly faster than that for probe (b), both emission ratios r were not significantly different when they plateaued.

Accordingly, this indicates that by introducing the endogenous targeting domain within IRS-1, the phosphorylation rate of probe (e) by the activated insulin receptor was enhanced, which demonstrated that the localized kinase signaling in the living cells can be visualized effectively using this probe for imaging protein phosphorylation.

Figure 6B:
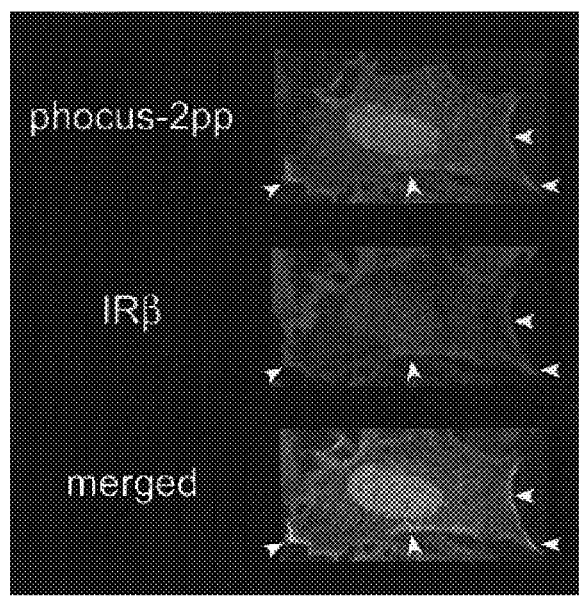

Insulin-stimulated co-localization of probe (e) and the insulin receptor at the plasma membrane were confirmed by the fluorescence images taken by the confocal laser scanning microscope (FIG. 6B). This membrane localization of probe (e) was not observed before insulin simulation. On the other hand, when probe (b) was used, no significant subcellular localization, including the plasma membrane, by insulin stimulation was observed (FIG. 4B).

From these results, it was demonstrated that the PH-PTB domain was ascribed to be responsible for the insulin-induced targeting of probe (e) to the membrane insulin receptor.

INDUSTRIAL APPLICABILITY

As described above in detail, the present invention provides a method for imaging signal transduction caused by protein phosphorylation within living cells. The present invention not only enables the visualization of kinase signal transduction within single live cells in high spatial and temporal resolution, but also enables the high-throughput screening of substances that regulate the activity of various phosphorylation and dephosphorylation substances. Further, by generating transgenic animals or plants using the probe for imaging protein phosphorylation of the present invention, a nondestructive continuous method for monitoring events related to signal transduction due to protein phosphorylation within target tissues and organs can be realized.

SEQUENCE LISTING

```
<160> NUMBER OF SEQ ID NOS: 3

<210> SEQ ID NO 1
<211> LENGTH: 13
<212> TYPE: PRT
<213> ORGANISM: Artificial Sequence
<220> FEATURE:
<223> OTHER INFORMATION: Description of Artificial Sequence:
      Synthesized Oligopeptide

<400> SEQUENCE: 1

Glu Thr Gly Thr Glu Glu Tyr Met Lys Met Asp Leu Gly
1               5                   10

<210> SEQ ID NO 2
<211> LENGTH: 11
<212> TYPE: PRT
<213> ORGANISM: Artificial Sequence
<220> FEATURE:
<223> OTHER INFORMATION: Description of Artificial Sequence:
      Synthesized Oligopeptide

<400> SEQUENCE: 2

Gly Asn Asn Gly Gly Asn Asn Asn Gly Gly Ser
1               5                   10

<210> SEQ ID NO 3
<211> LENGTH: 9
<212> TYPE: PRT
<213> ORGANISM: Artificial Sequence
<220> FEATURE:
<223> OTHER INFORMATION: Description of Artificiail Sequence:
      Synthesized Oligopeptide

<400> SEQUENCE: 3

Leu Pro Pro Leu Gly Arg Leu Thr Leu
1               5
```

Furthermore, it is suggested that upon insulin stimulation, SH2n within the probe for imaging protein phosphorylation preferentially binds via intramolecular reaction with the adjacent phosphorylated Y941 rather than binding via intermolecular reaction with the other localized phosphoproteins such as endogenous IRS proteins (*J. Biol. Chem.* 273, 29686-29692 (1998); *Mol. Endocrinol.* 14, 823-836 (2000))

The invention claimed is:

1. A probe for imaging protein phosphorylation and dephosphorylation, which comprises:
   (a) a peptide substrate domain containing a phosphorylation site having an amino acid residue selected from tyrosine, serine and threonine;
   (b) a phosphorylation recognition domain that is a single chain antibody obtained using the phosphorylated peptide substrate domain as an antigen, or an endogenous domain selected from SH2 domain, phosphotyrosine binding domain and WW domain, and specifically interacts and recognizes phosphorylation of the peptide substrate domain; and (c) a peptide linker sequence, wherein:

(i) the peptide substrate domain and the phosphorylation recognition domain are bound together by the peptide linker sequence and interposed between a donor chromophore and an acceptor chromophore that cause fluorescence resonance energy transfer (FRET) to occur; and (ii) the peptide substrate domain, the linker sequence and the phosphorylation recognition domain are linked in order from N-terminal to C-terminal of the probe.

2. The probe for imaging protein phosphorylation and dephosphorylation of claim 1, wherein the donor chromophore and the acceptor chromophore that cause FRET to occur, are fluorescent proteins each having different fluorescence wavelengths.

3. The probe for imaging protein phosphorylation and dephosphorylation of claim 1, wherein the donor chromophore and the acceptor chromophore that cause FRET to occur, are different color mutants of a green fluorescent protein.

4. The probe for imaging protein phosphorylation and dephosphorylation of claim 3, wherein the mutants of the green fluorescent protein are a cyan fluorescent protein and a yellow fluorescent protein.

5. The probe for imaging protein phosphorylation and dephosphorylation of claim 1, which comprises a localization sequence at a terminal end.

6. The probe for imaging protein phosphorylation and dephosphorylation of claim 1, wherein in the probe:

the donor chromophore and the acceptor chromophore that cause FRET to occur are selected from a cyan fluorescent protein and a yellow fluorescent protein, the linker sequence consists of the amino acid sequence of SEQ ID NO: 2, and the phosphorylation recognition domain is an N-terminal SH2 domain of p85 regulatory subunit of bovine phosphatidylinositol 3-kinase.

7. A method for screening substances that enhance or suppress protein phosphorylation, which comprises making the probe for imaging protein phosphorylation and dephosphorylation of claim 1 coexist with a candidate substance, measuring the change in efficiency of fluorescence resonance energy transfer (FRET) before and after addition of the candidate substance, comparing the efficiency of FRET before and after addition of the candidate substance, and identifying the substance that enhances or suppresses protein phosphorylation.

8. The method for screening substances that enhance or suppress protein phosphorylation of claim 7, wherein the probe for imaging protein phosphorylation and dephosphorylation and the candidate substance are made to coexist by introducing the probe for imaging protein phosphorylation and dephosphorylation into cells.

9. A method for screening substances that enhance or suppress protein dephosphorylation, which comprises making the probe for imaging protein phosphorylation and dephosphorylation of claim 1, wherein the substrate domain has been phosphorylated, coexist with a candidate substance, measuring the change in FRET efficiency before and after addition of the candidate substance, comparing the efficiency of FRET before and after addition of the candidate substance, and identifying the substance that enhances or suppresses protein dephosphorylation.

10. The method for screening substances that enhance or suppress protein dephosphorylation of claim 9, wherein the probe for imaging protein phosphorylation and dephosphorylation and the candidate substance are made to coexist by introducing the probe for imaging protein phosphorylation and dephosphorylation into cells.

11. A method for assaying an amount of a substance that enhances or suppresses protein phosphorylation, which comprises contacting the probe for imaging protein phosphorylation and dephosphorylation of claim 1 with various concentrations of a standard substance having a known enhancing or suppressing-ability to protein phosphorylation, and measuring fluorescence resonance energy transfer (FRET) efficiencies thereof to produce a calibration curve as a control, introducing the probe into cells, introducing a candidate substance that enhances or suppresses protein phosphorylation into the cells, measuring the change in FRET efficiency before and after of the candidate substance upon contacting the probe with the candidate substance in the cells, and determining the amount of the candidate substance by comparing the FRET efficiency of the candidate substance with the calibration curve.

12. A method for assaying an amount of a substance that enhances or suppresses protein phosphorylation, which comprises contacting the probe for imaging protein phosphorylation and dephosphorylation of claim 1 with various concentrations of the substance having a known enhancing or suppressing-ability to protein phosphorylation, and measuring fluorescence resonance energy transfer (FRET) efficiencies thereof to produce a calibration curve as a control, introducing the probe into cells, introducing the substance into the cells, measuring the change in FRET efficiency before and after addition of the substance upon contacting the probe with the substance in the cells, and determining the amount of the substance by comparing the FRET efficiency of the substance with the calibration curve.

* * * * *